(12) United States Patent
Bender et al.

(10) Patent No.: US 7,229,200 B1
(45) Date of Patent: Jun. 12, 2007

(54) LIGHT CONDUCTIVE ROD ELEMENTS AND LIGHT-DELIVERY TOOL INCLUDING A BASE FOR INTRODUCING LIGHT INTO A LIGHT CONDUCTIVE ROD ELEMENT

(75) Inventors: Thomas Bender, Auburn, NY (US); Anthony Cappabianca, Springfield, MA (US); John Hansson, Brooklyn, CT (US); Michael Weisser, Sturbridge, MA (US)

(73) Assignee: Schott Corporation, Elmsford, NY (US)

( * ) Notice: Subject to any disclaimer, the term of this patent is extended or adjusted under 35 U.S.C. 154(b) by 261 days.

(21) Appl. No.: 10/976,236

(22) Filed: Oct. 27, 2004

Related U.S. Application Data

(60) Provisional application No. 60/514,631, filed on Oct. 27, 2003.

(51) Int. Cl.
*F21W 131/202* (2006.01)

(52) U.S. Cl. .................. 362/573; 362/572; 362/556; 433/29

(58) Field of Classification Search .............. 362/556, 362/572–574, 558; 433/29; 602/93; 385/38
See application file for complete search history.

(56) References Cited

U.S. PATENT DOCUMENTS

| | | | |
|---|---|---|---|
| 2,932,294 A * | 4/1960 | Fourestier et al. | .......... 600/177 |
| 3,327,712 A * | 6/1967 | Kaufman et al. | .............. 606/40 |
| 4,004,143 A | 1/1977 | Good et al. | |
| 4,330,274 A | 5/1982 | Friedman et al. | |
| 4,334,863 A | 6/1982 | Magid et al. | |
| 5,003,434 A | 3/1991 | Gonser et al. | |
| 5,332,389 A | 7/1994 | Rosenstatter | |
| 5,908,295 A | 6/1999 | Kawata | |
| 6,304,712 B1 | 10/2001 | Davis | |
| 6,325,623 B1 | 12/2001 | Malnyk et al. | |
| 6,560,038 B1 | 5/2003 | Parkyn, Jr. et al. | |
| 6,688,763 B2 * | 2/2004 | Pameijer et al. | ............ 362/573 |
| 6,719,447 B1 | 4/2004 | Woodward et al. | |
| 6,739,744 B2 | 5/2004 | Williams et al. | |
| 6,932,599 B1 * | 8/2005 | Hartung | ....................... 433/29 |
| 2003/0091954 A1 | 5/2003 | West et al. | |

* cited by examiner

*Primary Examiner*—Laura Tso
(74) *Attorney, Agent, or Firm*—Louis J. Franco; Law Office of Louis J. Franco

(57) ABSTRACT

A light-conductive rod element includes a solid rod-shaped body having a side surface extending along a longitudinal rod axis between a first light-input end and a second light-redirecting end. The rod element is fabricated from a material exhibiting a refractive index greater than the refractive index of air in order to facilitate total internal reflection. The light-redirecting end includes at least a first planar face extending along a first plane definable by a first normal that is pitched with respect to the rod axis such that light propagating by total internal reflection between the first and second ends that impinges on the interface defined by the rod-element material and air at the first planar face is redirected by at least one of (i) reflection and (ii) refraction. Refracted components of light exit the rod body through the first planar face and reflected components of light exit the rod body through the side surface. The rod element is selectively coupleable with a handle that facilitates the selective introduction of light into the light-input end and, in combination with the handle, forms a light-delivery tool for delivering light to a region of interest.

20 Claims, 7 Drawing Sheets

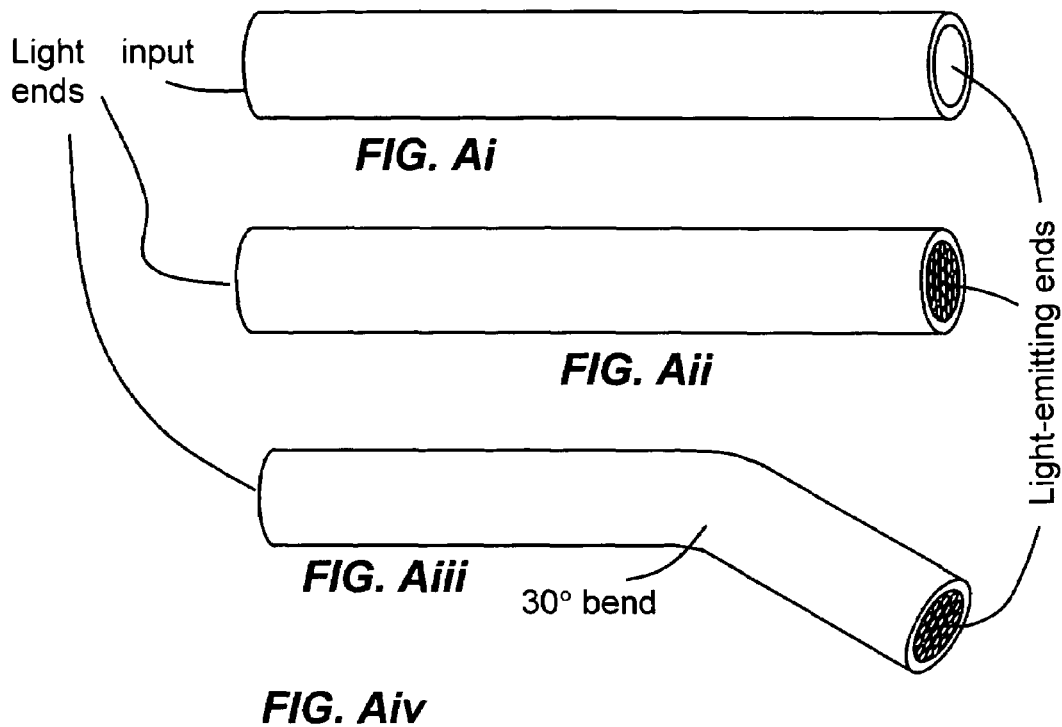
Illustrative elongated light-conductive elements selectively coupleable with light-generating handle/base
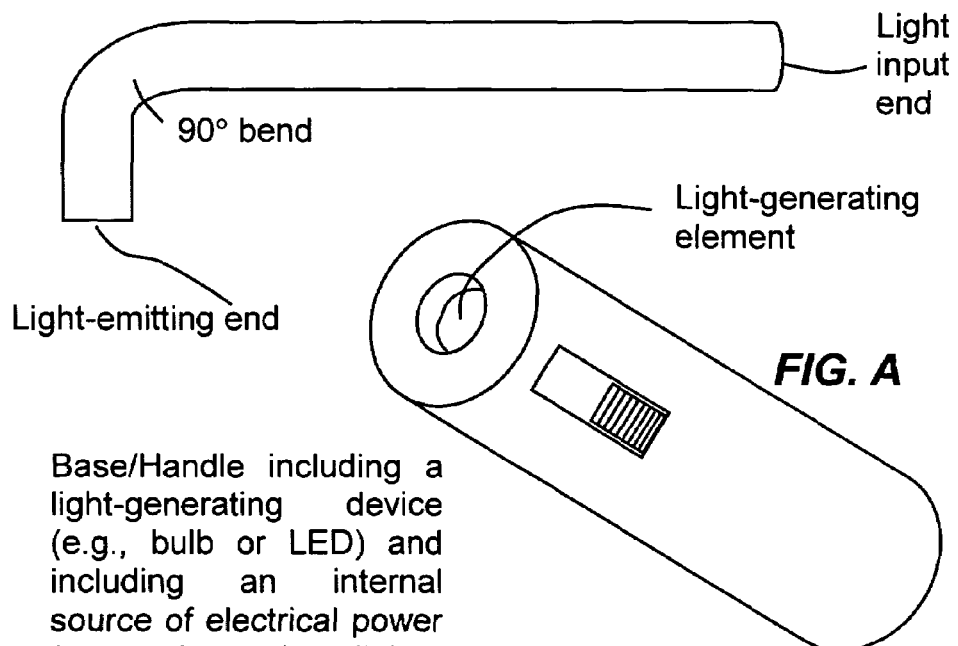
Background Art

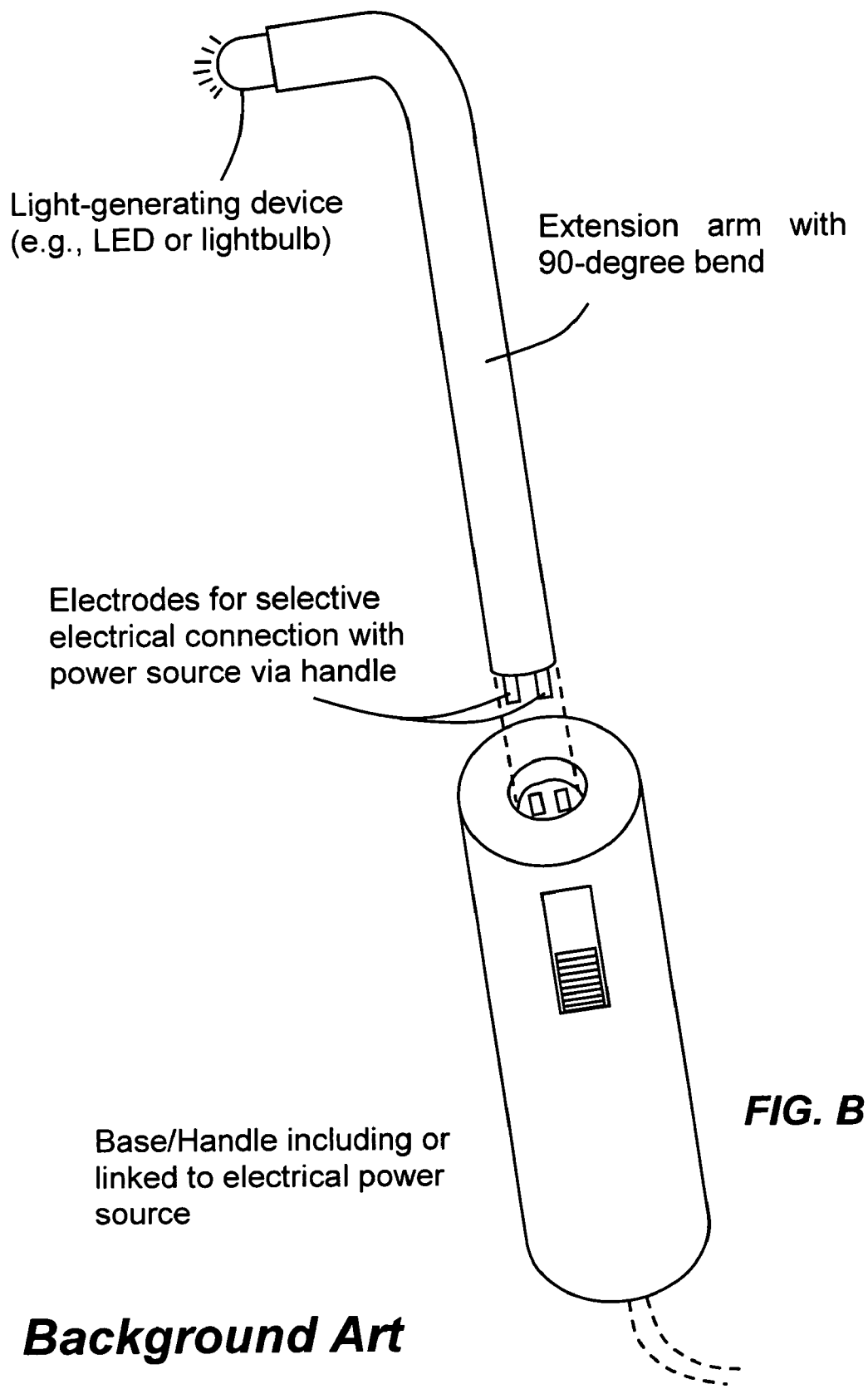
FIG. B
Background Art

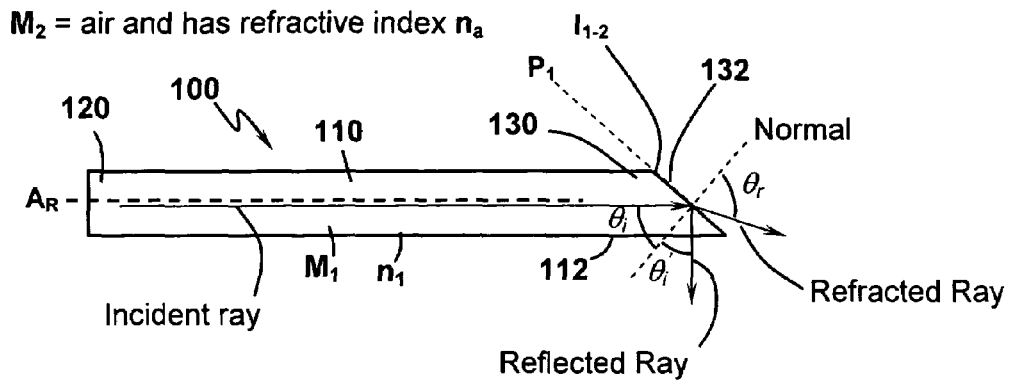
FIG. 1
Solid light-conducting rod made from material having refractive index $n_1 > n_2 = n_{air}$ and having single-plane exit face
FIG. 1A
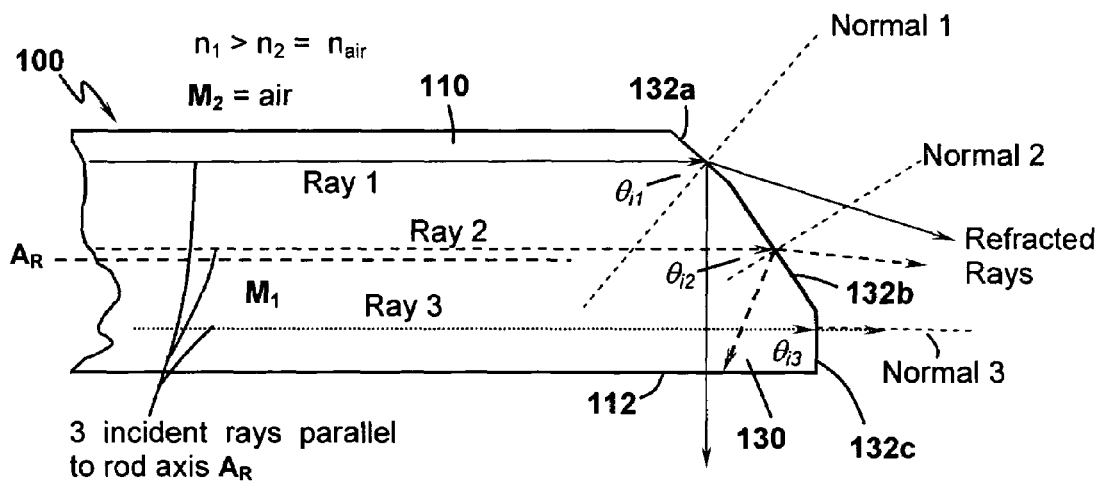

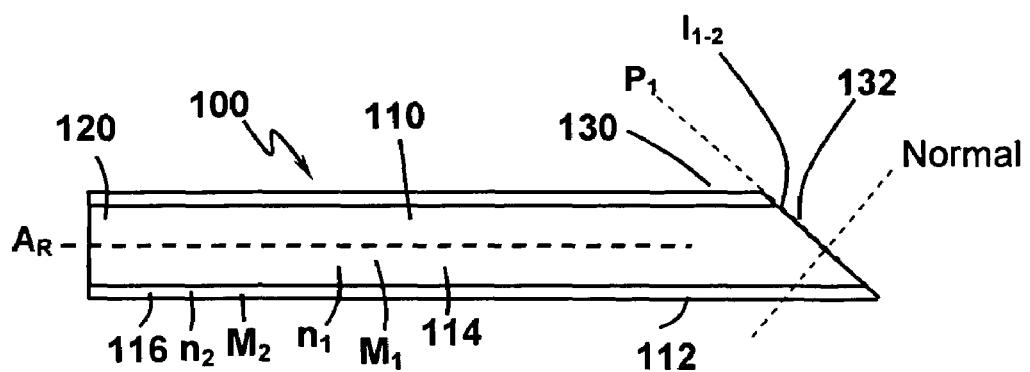
FIG. 2
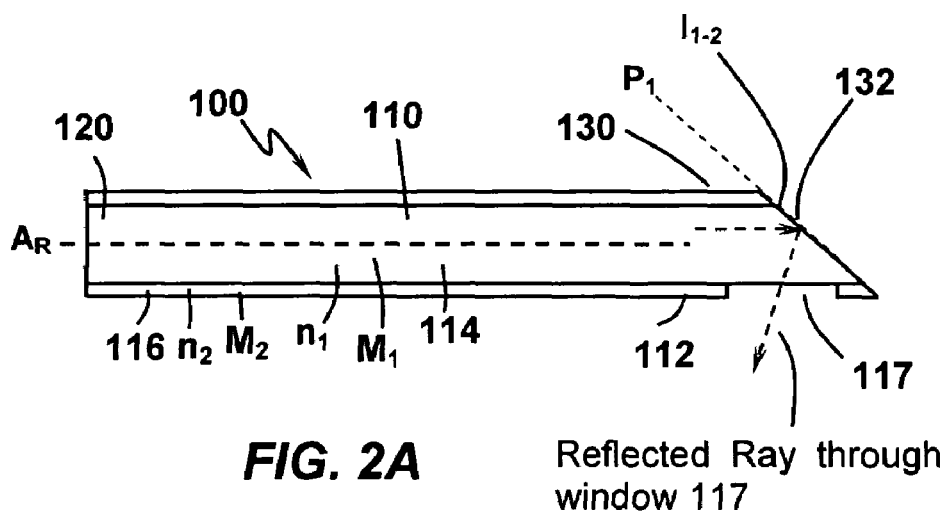
FIG. 2A  Reflected Ray through window 117
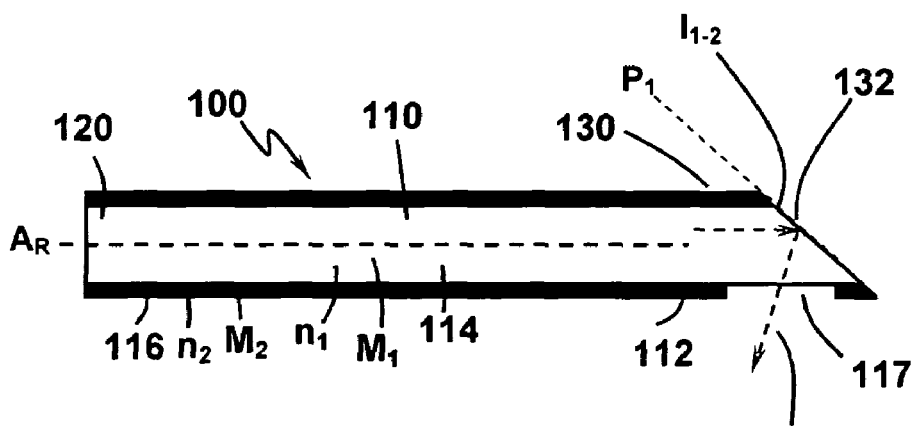
FIG. 2B  Reflected Ray through window 117 in blackened cladding 116

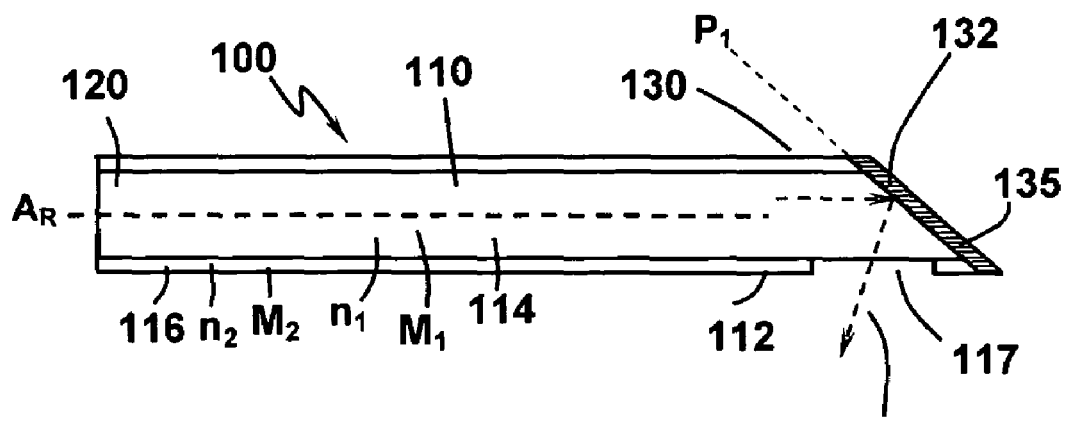
FIG. 2C  Reflected Ray through window 117
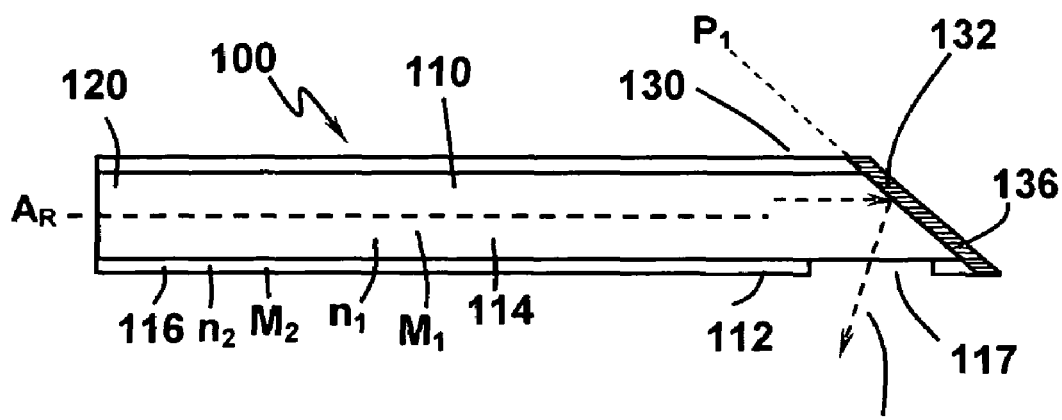
FIG. 2D  Reflected Ray through window 117

Optical connection 250 and/or electrical connection to at least one of (i) a remote light-emitting element 230 and (ii) an external electrical-power source 265

Electrical connection to an external electrical-power source 265 ns within a dental patient's mouth or the delivery of light energy to a dental-curing site in a patient's mouth, and, more particularly, to unbent light-transmissive elements adapted for the emission of light energy at any of various predetermined angles relative to the longitudinal axis of the light-conductive element.

LIGHT CONDUCTIVE ROD ELEMENTS AND LIGHT-DELIVERY TOOL INCLUDING A BASE FOR INTRODUCING LIGHT INTO A LIGHT CONDUCTIVE ROD ELEMENT

PROVISIONAL PRIORITY CLAIM

Priority based on Provisional Application Ser. No. 60/514,631, filed Oct. 27, 2003, and entitled "LIGHT CONDUCTIVE ROD ELEMENTS ADAPTABLE FOR USE IN DENTAL APPLICATIONS," is claimed.

BACKGROUND

1. Field

Although not so limited in its utility or scope, implementations of the present invention are particularly well suited for the selective illumination of regions of interests within a dental patient's mouth or the delivery of light energy to a dental-curing site in a patient's mouth, and, more particularly, to unbent light-transmissive elements adapted for the emission of light energy at any of various predetermined angles relative to the longitudinal axis of the light-conductive element.

2. Brief Description of Illustrative Environments and Related Art

Elongated light-conductive elements are applied to various applications in which remote, difficult-to-access regions require illumination or the delivery of electromagnetic energy for purposes other than illumination (e.g., photochemical curing). One field in which elongated light-conductive elements find use is the dental industry. More specifically, light-conductive elements are used to illuminate remote teeth and gums to facilitate drilling, filling, dental surgery and bleaching. Moreover, various bonding materials used in dentistry are photochemically cured by the delivery of light of an appropriate wavelength to the area to be bonded.

Currently, light-conductive elements exhibiting total internal reflection are used in the dental industry. Some such devices comprise single-element, light-conductive rods, while others comprise fused bundles of plural optical fibers. These devices typically include an elongated body having a first light-input end and a second light-emitting end opposite the light-input end. A typical dentist has a set of light conductive elements, each of which is selectively coupleable with a light-generating base, to accommodate the delivery of electromagnetic energy to different regions of interest within a patient's mouth. Alternative examples of light-generating bases include (i) a handle for retaining a light-conductive element and internally retaining a light-generating element and (ii) a handle that selectively retains a light conductive element and is optically connected to a unit, other than the handle, that houses a light-generating element, wherein the optical connection is provided, for example, through a flexible optical fiber bundle. A generic light-generating base and illustrative light-conductive elements for alternative use therewith are depicted in FIGS. A through Aiv. As shown, the various elements of a set may be characterized by different angles of emission relative to the propagation axis of the input energy. Light emission at various angles is facilitated by bent and/or curved optical rods. Some rods are straight while others may include bends of 30, 45, 60 or 90 degrees, for example. As known to those skilled in the art of optical fiber component manufacturing, for example, the fabrication of bent optical rods is substantially more expensive than the fabrication of straight rods, for instance. The cost of fabricating bent rods of various angles is passed on to the dental professional and, ultimately, the patient or patients' insurers.

A second general type of illumination tool currently used by dental professionals is represented in FIG. B and includes an extension arm having opposed base and distal ends. The base end is selectively connectable to a base that serves as a handle and either includes an internally-contained source of electrical power (e.g., a battery) or is selectively connectable to a source of electrical power external to the base. The distal end of the extension arm includes a light-generating device such as an LED or light bulb and the extension arm houses electrical conduits (e.g., wires) for including the light-generating device in an electrical circuit that can be selectively opened and closed by a switch in the handle to alternatively shut down and illuminate the light-generating device. These types of dental illumination tools require the dental professional to possess variously configured extension arms, each of which extension arms includes its own light-generating device and set of electrodes for coupling with the power-supplying handle. Moreover, although these illumination tools are generally low-power devices, the inclusion of the light-generating device at the distal end of an extension arm necessarily involves introducing a portion of the electrical circuit into a patient's mouth. Accordingly, the extension arm, and the portion of the circuitry contained therein must endure autoclaving procedures after use. Moreover, dental illumination tools in which a single light-generating element is relied upon to alternatively deliver light through any of various conduits, such as the illumination tools of the first type previously discussed, are decidedly advantageous from a maintenance perspective relative to illumination tools of the second type.

Accordingly, there exists a need for less costly elongated, light-conductive elements adaptable for use in dental applications. More specifically, there exists a need for light-conductive elements that can distribute light at various predetermined angles without requiring the fabrication of multiple bent light-conductive elements.

SUMMARY

The present invention is generally directed to elongated, light-conductive elements and, more specifically in various embodiments, to straight (i.e. non-bent or unbent) elongated light-conductive elements adapted for the emission of light energy at any of various predetermined angles relative to the longitudinal axis of the light-conductive element.

Each of various embodiments of an elongated light-conductive element includes a solid, unclad, translucent rod-shaped body formed from a first material characterized by a first refractive index greater than the refractive index of air. For purposes of the specification and claims, "translucent" is defined in its broadest sense to include transparent and semi-transparent materials (i.e., all materials that are not opaque). Moreover, "light" includes a broad range of wavelengths within the electromagnetic spectrum and is not limited to visible electromagnetic wavelengths. The rod extends along a longitudinal rod axis between a first light-input end and a second light-redirecting end longitudinally opposite the light-input end. The light-redirecting end assumes various alternative configurations and physical properties in various versions depending on the desired light-redirecting effect. The desired light-redirecting effect of a particular embodiment is achieved by at least one of refraction and reflection rather than by bends or curves in the rod. In unclad versions, air is relied upon as a second optical medium having a second refractive index lower than the refractive index of the rod to facilitate propagation by total internal reflection between the light-input and light-redirecting ends of the rod.

Each embodiment of one selected set of unclad versions is adapted for cooperative coupling with a handle base that includes a light-generating element such as a light bulb or light-emitting diode (LED), for example. The handle either includes an internal source of electrical power (e.g., a battery) or is selectively connectable to an external source of electrical power to facilitate selective illumination of the light-generating element via a switch, for example. The rod is cooperatively coupleable with the handle base such that, when the light-generating element is illuminated, light is caused to enter the light-input end of the rod and propagate through the rod for impingement on the light-redirecting end of the rod where it is redirected in accordance with a predetermined light-redirecting scheme.

In accordance with an alternative design, the rod-shaped body includes a light-generating element located closer to the light-input end than to the light-redirecting end. In an embodiment designed accordingly, the rod is cooperatively coupleable with a handle base that retains the rod and selectively provides electrical power to the light-generating element included in or on the rod.

An alternative set of embodiments includes a solid rod-shaped elongated body clad by a second material having a second index of refraction lower than the first index of refraction characteristic of the material from which the rod is formed. In some aspects, the second material is at least partially blackened which facilitates the prevention of at least one of (i) the undesired escape through the side surface of light input into the light-input end of the rod and (ii) the introduction of undesirable ambient light from the environment surrounding the clad rod body. As is more fully described in the detailed description, some embodiments facilitate the reflection of light off a reflective face at the light-redirecting end of the rod and through a side wall of the rod. In some versions in which the rod is clad and blackened, a section of the side wall is non-blackened to facilitate the efficient exit of reflected light through the side wall.

In each of various versions comprising a solid unclad or clad rod, the rod exhibits one of any of various cross-sectional geometries as viewed into a plane perpendicular to the rod axis including, by way of non-limiting example, circular, elliptical, square or other rectangular shape, hexagonal, octagonal and any of a variety of irregular polygonal shapes. Moreover, the desired reflection and/or refraction effects are achieved, in various aspects, by a light-redirecting end including at least one face extending along a plane definable in part by a normal that is pitched with respect to the rod axis. Some versions include a plurality of at least two planar faces extending along distinct planes to facilitate correspondingly plural reflection/refraction effects. Also within the scope and contemplation of the invention are rods having light-redirecting faces including curved surfaces in addition, for example, to the at least one pitched planar face.

Representative implementations are more completely described and depicted in the following detailed description and the accompanying drawings.

BRIEF DESCRIPTION OF THE DRAWINGS

FIG. A shows a handle base including a light-generating element for use with bent light-conductive rods of a type previously and currently utilized in dental applications;

FIGS. Ai through Aiv depict illustrative examples of light-conductive rods lacking light-redirecting emitting ends wherein light redirection, where applicable, is achieved by a bend in the light-conductive rod;

FIG. 1 depicts a side view an elongated, unclad light-conductive rod having a light-emitting end with a single planar face lying in a plane pitched with respect to the longitudinal axis of the rod;

FIG. 1A shows a side view of a light-conductive rod having a light-emitting end defined by three planar faces extending along three correspondingly distinct planes each of which faces facilitates a unique set of reflection/refraction and transmission effects;

FIG. 2 depicts a light-conductive rod body comprising a core made from a first material and a cladding made from a second material;

FIG. 2A illustrates a clad rod body including a window in the cladding that permits the exit of light reflected within the rod body through the side surface of the rod body without the light's encountering cladding material;

FIG. 2B depicts an embodiment similar to the embodiment of FIG. 2A wherein the cladding is selectively blackened;

FIG. 2C shows a version of a rod body similar to the version of FIG. 2A in which the light-redirecting end of the rod body is coated with a reflective material;

FIG. 2D shows a version of a rod body similar to the version of FIG. 2A in which a reflective element has been affixed to the light-redirecting end of the rod body.

DETAILED DESCRIPTION

Figure 3:
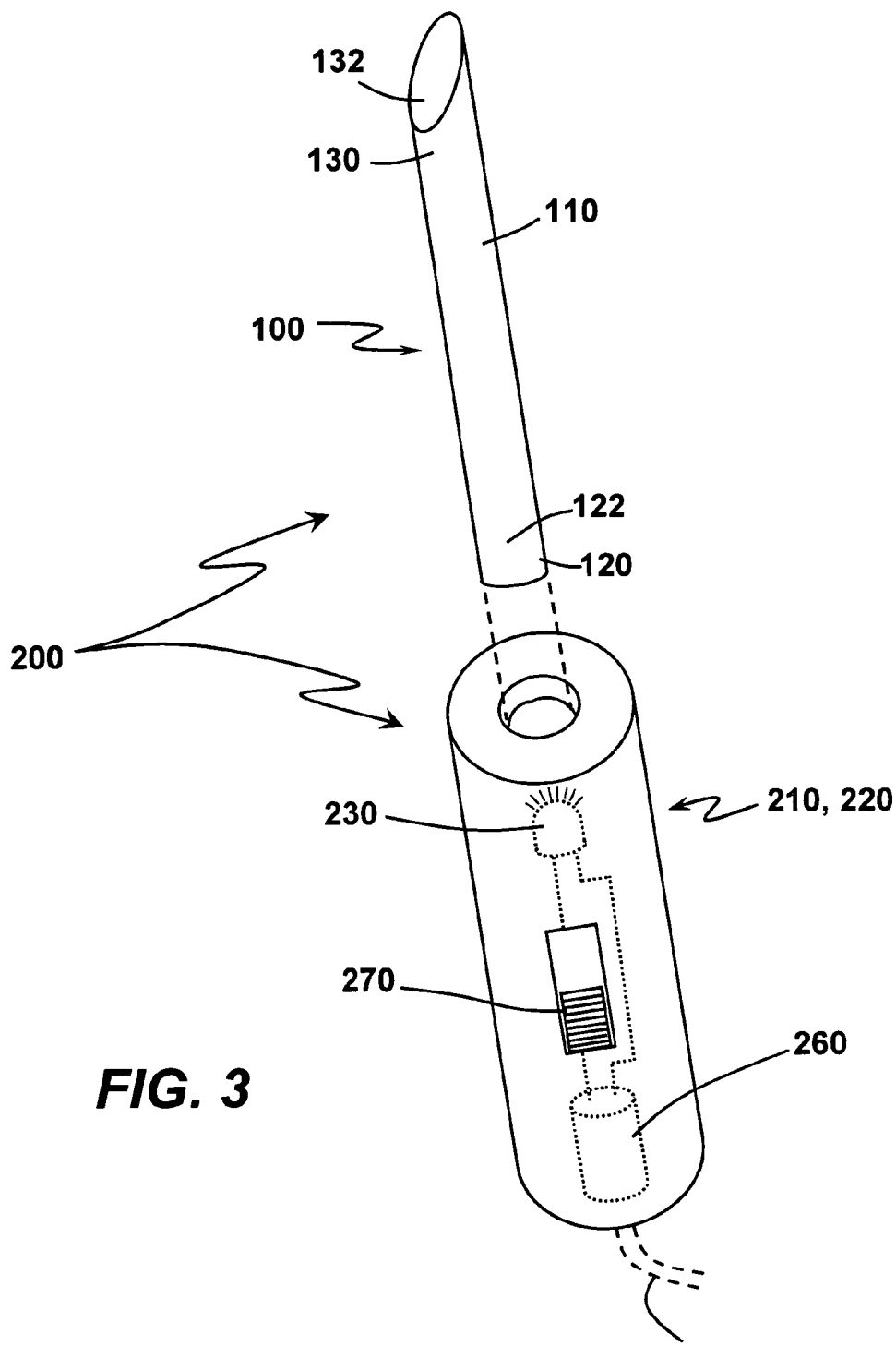
FIG. 3 depicts a light-delivery tool for delivering light to a region of interest and including a light-conductive rod element selectively coupleable with a handle adapted for introducing light into the light-input end of the light-conductive rod element.

The following description of illustrative embodiments of elongated light-conductive rod elements is demonstrative in nature and is not intended to limit the invention or its application of uses. The various implementations, aspects, versions and embodiments described in the summary and detailed description are in the nature of non-limiting examples falling within the scope of the appended claims and do not serve to define the maximum scope of the claims.

Referring to FIG. 1, an illustrative elongated light-conductive rod element 100 comprises a solid, unclad, translucent rod-shaped body 110 fabricated from a first material $M_1$ characterized by a first refractive index $n_1$ greater than the refractive index of air $n_a$. The elongated rod body 110 extends unbent along a longitudinal rod axis $A_R$ and is defined in part by a side surface 112 that extends between a first light-input end 120 and a second light-redirecting end 130 longitudinally opposite the light-input end 120. The light-redirecting end 130 of the illustrative embodiment of FIG. 1 comprises a planar surface 132 that extends along a plane $P_1$ having an orientation definable by an axis orthogonal to the plane (also referred to as "normal") which normal axis is pitched at a predetermined angle $\theta_t$ with respect to the rod axis $A_R$. That is, the planar surface 132 is oriented obliquely with respect to the rod axis $A_R$ and, because the rod body 110 is straight, the rod axis $A_R$ passes through the planar surface 132.

As stated in the summary, the light-redirecting end 130 of a particular embodiment is configured in accordance with the desired light-redirecting effect. Moreover, the desired light-redirecting effect of a particular embodiment is achieved by at least one of (i) refraction and (ii) reflection rather than by bends or curves in the rod body 110. In the particular version of FIG. 1, the predetermined angle $\theta_i$ facilitates partial refraction and partial reflection of light that propagates through the rod body 110 and impinges upon the optical interface $I_{1-2}$ (hereinafter "interface $I_{1-2}$".) defined by the first material and air at the first planar face 132. In the unclad version of FIG. 1, because air constitutes a second material $M_2$ having a second refractive index $n_2$ ($=n_a$) lower than the refractive index $n_1$ of the rod, propagation of light through the rod body 110, and along the rod axis $A_R$, by total internal reflection is facilitated. Moreover, as shown in the ray-trace aspects of FIG. 1, and in accordance with Snell's law, light incident upon the interface $I_{1-2}$ with an orientation parallel to the rod axis $A_R$ is refracted away from the normal in passing from the material of higher refractive index (i.e., $M_1$) to the material of lower refractive index (i.e., $M_2$=air). The reflected light is, in accordance with the law of reflection, internally reflected from the interface $I_{1-2}$ at an angle $\theta_i$ with respect to the normal that is equal in magnitude to the incident angle $\theta_i$. It will be appreciated by those of ordinary skill in the optical arts that the pitch of the plane $P_1$ with respect the rod axis $A_R$ can be altered to facilitate corresponding alternations in the reflection-transmission ratio between a theoretical first extreme in which there is total transmission (e.g., when the normal is parallel to the rod axis) and a second extreme in which there is total (internal) reflection (e.g., when $\theta_i$>critical angle $\theta_c$).

Referring to FIG. 1A, an elongated rod body 110 extends along a longitudinal rod axis $A_R$ and includes a "faceted" light-redirecting end 130 comprising three planar faces 132a, 132b and 132c extending along three distinct planes (not labeled). Illustrative incident rays 1, 2 and 3, each of which is parallel to the rod axis $A_R$, are shown to impinge upon, respectively, first, second and third planar faces 132a, 132b and 132c. The first, second and third normals 1 and 2 and 3 defining the first, second and third planes along which, respectively, faces 132a, 132b and 132c extend are disposed at angles $\theta_{i1}$, $\theta_{i2}$ and $\theta_{i3}$ with respect to the rod axis $A_R$ and $\theta_{i1}$>$\theta_{i2}$>$\theta_{i3}$, with $\theta_{i3}$=0°. Transmitted and reflected rays corresponding to each of incident rays 1, 2 and 3 are qualitatively represented to generally illustrate the expected behavior of incident light in such an embodiment. It will be appreciated that these variously pitched planar faces 132a, 132b and 132c not only cause light incident thereupon to be redirected at different angles, but also cause light incident thereupon to exhibit different reflection-transmission ratios. For instance, the most intense transmitted light is the light transmitted through face 132c, while the most intense reflected light is that reflected from the interface defined by face 132a and the air surrounding the rod body 110. The transmission of light of predetermined intensities through the light-redirecting end 130 and through the side wall 112 facilitates the impingement of light on external regions of interest generally in front of the light-redirecting end 130 and to the side of the rod body 110. The resultant versatility of such an embodiment will find use, for example, in dental applications for the directing of illuminating and/or photo-chemical-curing wavelengths to regions of a dental patience's mouth that are more difficult to access with bent light-conducting rods such as those shown in FIGS. Aiii and Aiv. However, instruments utilizing such embodiments will find use in other industries requiring illumination of difficult-to-access regions of interest including, by way of non-limiting example, the medical profession more generally and the plumbing, electrical, construction and mechanical trades.

FIGS. 2 through 2C depict various alternative embodiments in which the rod body 110 comprises a core 114 of a first material $M_1$ having a first refractive index n1 and a cladding 116 of a second material $M_2$ having a second refractive index $n_2$ that is lower than the first refractive index $n_1$. FIG. 2 is a clad version in which the cladding 116 is co-extensive with the core 114. In contrast, the clad version of FIG. 2A includes a window 117 in the cladding 116 in the vicinity in which light reflected from the interface $I_{1-2}$ between the core 114 and the surrounding air exits the side surface 112 of the rod body 110. The window 117 represents an absence of cladding 116, thereby giving the reflected light one less layer of material to pass through in exiting the rod body 110, which reduces absorption and obviates the light's passing through an additional refracting interface (i.e., the interface defined between the core 114 and the cladding 116). The window 117 may be created by any of various alternative methods including, by way of example, physically or chemically etching away the cladding 116 in the region desired.

In another set of alternative embodiments, at least a portion of the rod body 110 is selectively blackened by a process such as hydrogen firing, for example. Blackening by hydrogen firing itself is a process known to those of ordinary skill in the art of optical component fabrication; accordingly, details of the process are omitted from this description. It will also be appreciated by those of ordinary skill in the art that "blackening" is used throughout the specification and claims in a broad, informal sense and includes, for example, darkening other than strictly blackening such as darkening that manifests itself in various shades of brown or gray by way of non-limiting example. More specifically, "blacken," "blackened" and "blackening" should be read and interpreted as broadly as "darken," "darkened," and "darkening" regardless of actual color and shade characteristics. Suggestions as to where to blacken include blackening adjacent the side surface 112 of the rod body 110 regardless of whether the rod body 110 includes both a core 114 and a cladding 116. Those skilled in the art will appreciate that selective blackening facilitates the prevention of at least one of (i) the undesired (e.g., premature) escape of light input into the light-input end 120 of the rod body 110 and (ii) the introduction into the rod body 110 of undesirable ambient light from the environment surrounding the rod body 110. Depicted in FIG. 2B is an illustrative embodiment including selectively blackened cladding 116.

Additional alternative embodiments include selective application of a reflective coating 135 to the light-redirecting end 130 of the rod body 110. Such a coating 135 is alternatively applied directly to the material from which the rod body 110 is fabricated or to a reflective element 136 that is in turn attached to the light-redirecting end 130 of the rod body 110. It will be appreciated that a reflective coating 135 is typically applied to facilitate total or near-total reflection. FIG. 2C depicts an illustrative embodiment in which a reflective coating 135 has been applied to the planar face 132 at the light-redirecting end 130 of a rod body 110. FIG. 2D depicts an embodiment in which a reflective element 136 is affixed to the light-redirecting end 130 or the rod body 110.

FIG. 3 shows a light-delivery tool 200 for delivering light to a region of interest. The light-delivery tool 200 includes a light-conductive rod element 100, variously configured as previously described, in combination with a base 210 that, in the case illustrated, is in the form of a handle 220. The handle 220 is adapted for the selective retention of the light-conductive rod element 100 and facilitates the introduction of light emitted from a selectively illuminable light-generating element 230 into the light-input end 120 of the light-conductive rod element 100. In various versions, as represented omnibusly by FIG. 3, the light-generating element 230 is either (i) housed by the handle 220 or (ii) remotely located from the handle 220 and optically connected thereto in order to facilitate the introduction of light emitted therefrom into the light-input end 120 of the light-conductive rod element 100. As known to those of ordinary skill in the relevant arts, the optical connection may be provided by a flexible optical fiber bundle 250, for example. In addition, the handle 220 one of (i) houses a source of electrical power, such as a battery 260 and (ii) is electrically connectable to an external electrical-power source 265 (e.g., AC outlet or external battery or DC power supply). When all elements are operatively arranged, light is selectively deliverable through the light-conductive rod element 100 by, for example, the activation of a switch 270 included on the handle 220. It is to be understood that, although the handle 220 is shown as a generic device in FIG. 3, it can take various forms. For instance, the light-conducive rod element 100 may be incorporated into the extension arm of a dental drill (not shown) or other dental or surgical implement having a handle to which the light-conductive rod element 100 is connected.

Figure 4:
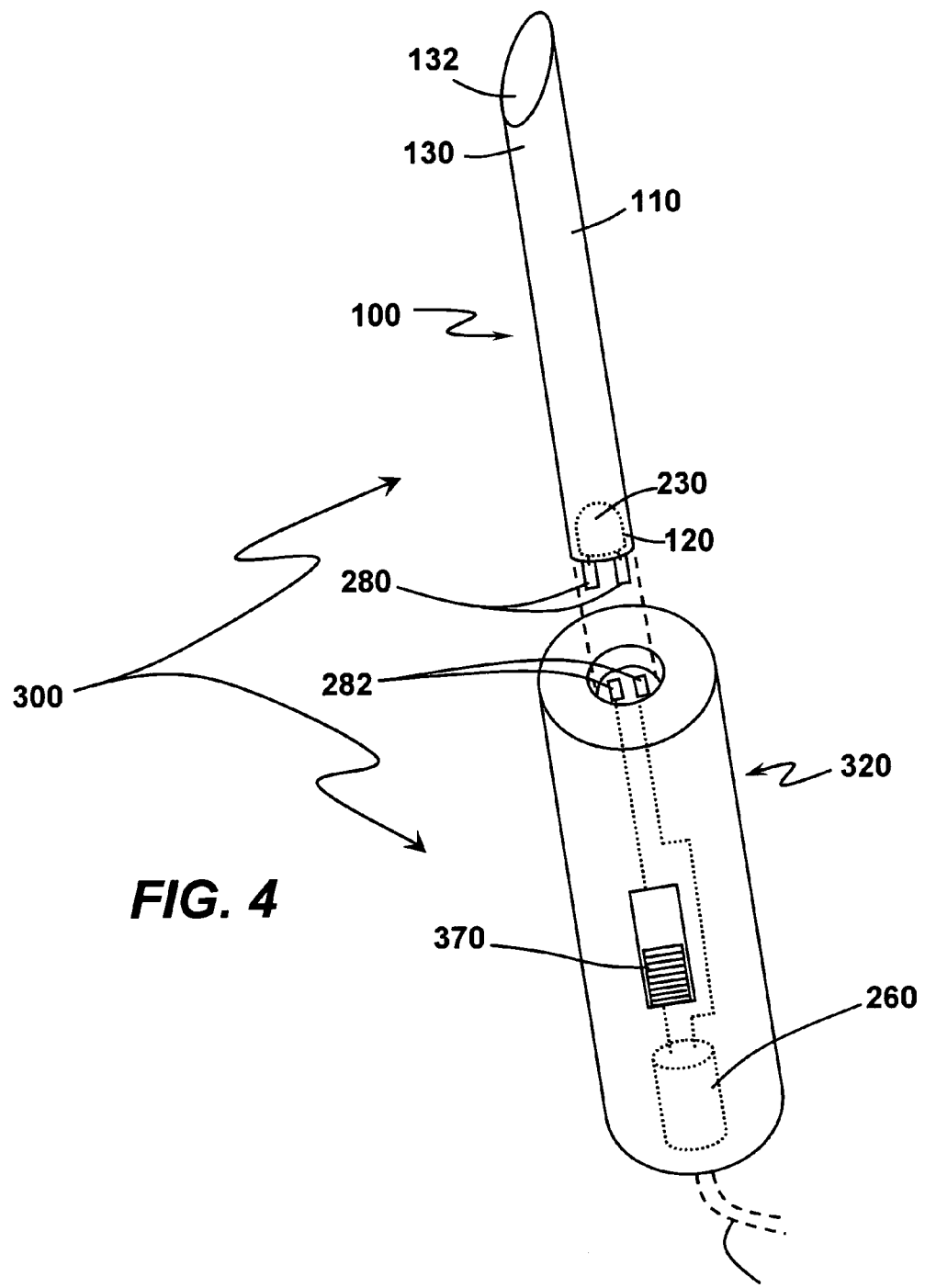
FIG. 4 depicts a version of a light-conductive rod including a light-generating element proximate the light-input end of the rod body and selectively coupleable with a handle adapted for supplying electrical power to the light-generating element.

The illustrative embodiments thus far described in the detailed description are adapted for selective cooperative coupling with a base 210 in the form of a handle 220 including or operatively linked to a light-generating element 230 as shown, for example, in FIG. 3. FIG. 4 shows an illustrative embodiment in which a light-generating element 230 is incorporated in the rod body 110 of the elongated light-conductive element 100. Typically, as with the version depicted, the light-generating element 230 is located proximate the light-input end 120 of the rod body 110. The rod body 110 including a light-generating element 230 is selectively coupleable with, and retainable by, a handle 320 to form a light-delivery tool 300 for delivering light to a region of interest. The handle 320 either includes (e.g., houses) an internal electrical-power source 260 (e.g., a battery) or is selectively connectable to an external electrical-power source 265 (e.g., an electrical outlet). When the rod body 110 is cooperatively coupled with the handle 320, electrical communication between the power source and the light-generating element 230 is established or selectively establishable through a switch 370. When the light-conductive rod element 100 including a light-generating element 230 is operatively coupled with the handle 320, the light-generating element 230 is brought into electrical connection with circuit elements (e.g., switch 270, power source 260 or 265, etc.) through electrical contacts such as prongs 280 that plug into a socket 282 by way of non-limiting example.

The foregoing is considered to be illustrative of the principles of the invention. Furthermore, since numerous modifications and changes will readily occur to those skilled in the art, it is not desired that the foregoing limit the invention to the exact construction and operation shown and described. Accordingly, all suitable modifications and equivalents may be resorted to that appropriately fall within the scope of the invention as expressed in the appended claims.

What is claimed is:

1. A light-conductive rod element comprising:
a straight and solid rod body having a side surface extending along a longitudinal rod axis between a first light-input end and a second light-redirecting end between which the rod body is capable of propagating light by total internal reflection, the rod body being fabricated from a translucent first material characterized by a first refractive index greater than the refractive index of air, wherein (i) the light-redirecting end includes at least a first planar face extending along a first plane definable in part by a first normal that is pitched with respect to the rod axis, (ii) when the first planar face is in contact with air, there is defined by the first material and the air an optical interface at the first planar face, and (iii) the first normal defines with the rod axis an angle such that at least a portion of light caused to propagate along the rod axis by total internal reflection between the first and second ends, and impinge on the optical interface at the first planar face, is redirected by internal reflection at the optical interface and caused to exit the rod body through the side surface.

2. The light-conductive rod element of claim 1 wherein the rod body is adapted for selective coupling with, and retention by, a handle that one of (i) houses a selectively illuminable light-generating element and (ii) is optically connected to a light-generating element external to the handle for the selective introduction of light into the light-input end of the rod body.

3. The light-conductive rod element of claim 1 further comprising a selectively illuminable light-generating element incorporated in the rod body in a location more proximate the light-input end than the light-redirecting end.

4. The light-conductive rod element of claim 1 wherein at least a portion of light caused to propagate along the rod axis by total internal reflection, and impinge upon the optical interface at the first planar face, is refracted and exits the rod body through the first planar face.

5. The light-conductive rod element of claim 1 wherein the first material constitutes a core and the rod body further includes a cladding fabricated from a second material having a second refractive index lower than the first refractive index.

6. The light-conductive rod element of claim 5 wherein the light-conductive rod element further includes a window in the cladding in the vicinity in which light reflected from the interface defined at the first planar face exits the side surface of the rod body thereby obviating at least a portion of the reflected light's passing through a refracting interface defined between each of the core and the cladding and the cladding and the surrounding air.

7. The light-conductive rod element of claim 6 wherein at least a portion of the cladding is blackened in order to facilitate the prevention of at least one of (i) the undesired escape through the side surface of light input into the light-input end of the rod and (ii) the introduction of undesirable ambient light from the environment surrounding the clad rod body.

8. The light-conductive rod element of claim 5 wherein at least a portion of the cladding is blackened in order to facilitate the prevention of at least one of (i) the undesired escape through the side surface of light input into the light-input end of the rod and (ii) the introduction of undesirable ambient light from the environment surrounding the clad rod body.

9. The light-conductive rod element of claim 1 wherein the light-redirecting end includes at least two planar faces extending along distinct planes definable by first and second normals pitched at different angles with respect to the longitudinal rod axis such that light caused to propagated along the rod axis by total internal reflection and impinge upon the first face is redirected at a different angle, with a different reflection-transmission ratio, than light caused to propagated along the rod axis by total internal reflection and impinge upon the second face.

10. The light-conductive rod element of claim 9 wherein the rod body is adapted for selective retention by a handle that one of (i) houses a selectively illuminable light-generating element and (ii) is optically connected to a light-generating element external to the handle for the selective introduction of light into the light-input end of the rod body.

11. A light-delivery tool for delivering light to a region of interest, the tool comprising:

a solid light-conductive rod element including an elongated rod body having a side surface extending along a longitudinal rod axis between a first light-input end and a second light-redirecting end between which the rod body is capable of propagating light by total internal reflection, the rod body being fabricated from a translucent first material characterized by a first refractive index greater than the refractive index of air, wherein (i) the light-redirecting end includes at least a first planar face extending along a first plane definable in part by a first normal that is pitched with respect to the rod axis, (ii) when the first planar face is in contact with air, there is defined by the first material and the air an optical interface at the first planar face, and (iii) the first normal defines with the rod axis an angle such that at least a portion of light caused to propagate along the rod axis by total internal reflection between the first and second ends, and impinge on the optical interface at the first planar face, is redirected by internal reflection at the optical interface and caused to exit the rod body through the side surface; and a handle adapted for selective retention of the light-conductive rod element, the handle facilitating the introduction of light emitted from a selectively illuminable light-generating element into the light-input end of the light-conductive rod element, wherein the light-generating element is one of (i) housed by the handle and (ii) optically connected to the handle.

12. The light-delivery tool of claim 11 wherein at least a portion of light caused to propagate along the rod axis by total internal reflection, and impinge upon the optical interface at the first planar face, is refracted and exits the rod body through the first planar face.

13. The light-delivery tool of claim 11 wherein the light-conductive rod element constitutes a core and the rod body further includes a cladding fabricated from a second material having a second refractive index lower than the first refractive index.

14. The light-delivery tool of claim 13 wherein at least a portion of the cladding of the light-conductive rod element is blackened in order to facilitate the prevention of at least one of (i) the undesired escape through the side surface of light input into the light-input end of the rod and (ii) the introduction of undesirable ambient light from the environment surrounding the clad rod body.

15. A light-delivery tool for delivering light to a region of interest, the tool comprising:

a solid light-conductive rod element including an elongated rod body having a side surface extending along a longitudinal rod axis between a first light-input end and a second light-redirecting end between which the rod body is capable of propagating light by total internal reflection, the rod body being fabricated from a translucent first material characterized by a first refractive index greater than the refractive index of air, wherein (i) the light-redirecting end includes at least a first planar face extending along a first plane definable in part by a first normal that is pitched with respect to the rod axis, (ii) when the first planar face is in contact with air, there is defined by the first material and the air an optical interface at the first planar face, and (iii) the first normal defines with the rod axis an angle such that at least a portion of light caused to propagate along the rod axis by total internal reflection between the first and second ends, and impinge on the optical interface at the first planar face, is redirected by internal reflection at the optical interface and caused to exit the rod body through the side surface, wherein the light-conductive rod element further includes, adjacent the light-input end, a selectively illuminable light-generating element; and a handle adapted for selective coupling with, and retention of, the light-conductive rod element, the handle facilitating the selective supply of electrical power to the selectively illuminable light-generating element and one of (i) housing an internal electrical-power source and (ii) being selectively connectable to an external electrical-power source.

16. The light-delivery tool of claim 15 wherein at least a portion of light caused to propagate along the rod axis by total internal reflection, and impinge upon the optical interface at the first planar face, is refracted and exits the rod body through the first planar face.

17. The light-delivery tool of claim 15 wherein the light-conductive rod element constitutes a core and the rod body further includes a cladding fabricated from a second material having a second refractive index lower than the first refractive index.

18. The light-delivery tool of claim 17 wherein at least a portion of the cladding of the light-conductive rod element is blackened in order to facilitate the prevention of at least one of (i) the undesired escape through the side surface of light input into the light-input end of the rod and (ii) the introduction of undesirable ambient light from the environment surrounding the clad rod body.

19. The light-delivery tool of claim 17 wherein at least a portion of light caused to propagate along the rod axis by total internal reflection, and impinge upon the optical interface at the first planar face, is refracted and exits the rod body through the first planar face.

20. The light-conductive rod element of claim 15 wherein the light-redirecting end includes at least two planar faces extending along distinct planes definable by first and second normals pitched at different angles with respect to the longitudinal rod axis such that light caused to propagated along the rod axis by total internal reflection and impinge upon the first face is redirected at a different angle, with a different reflection-transmission ratio, than light caused to propagated along the rod axis by total internal reflection and impinge upon the second face.

* * * * *